(12) United States Patent
Zhao et al.

(10) Patent No.: US 11,766,409 B2
(45) Date of Patent: Sep. 26, 2023

(54) CORE-SHELL POLYMER NANOPARTICLE

(71) Applicant: THE UNIVERSITY OF QUEENSLAND, St Lucia (AU)

(72) Inventors: Chunxia Zhao, St Lucia (AU); Yun Liu, St Lucia (AU)

(73) Assignee: The University of Queensland, St. Lucia (AU)

( * ) Notice: Subject to any disclaimer, the term of this patent is extended or adjusted under 35 U.S.C. 154(b) by 0 days.

(21) Appl. No.: 17/059,770

(22) PCT Filed: May 31, 2019

(86) PCT No.: PCT/AU2019/050557
§ 371 (c)(1),
(2) Date: Nov. 30, 2020

(87) PCT Pub. No.: WO2019/227169
PCT Pub. Date: Dec. 5, 2019

(65) Prior Publication Data
US 2021/0205232 A1 Jul. 8, 2021

(30) Foreign Application Priority Data
May 31, 2018 (AU) ................................ 2018901933

(51) Int. Cl.
*A61K 31/137* (2006.01)
*A61K 9/51* (2006.01)
*A61K 47/69* (2017.01)
*A61K 31/12* (2006.01)
*A61K 31/135* (2006.01)
*A61K 31/192* (2006.01)
*A61K 31/337* (2006.01)
*A61K 31/7048* (2006.01)
*A61K 45/06* (2006.01)
*B82Y 5/00* (2011.01)
*B82Y 40/00* (2011.01)

(52) U.S. Cl.
CPC .......... *A61K 9/5192* (2013.01); *A61K 9/5146* (2013.01); *A61K 31/12* (2013.01); *A61K 31/135* (2013.01); *A61K 31/192* (2013.01); *A61K 31/337* (2013.01); *A61K 31/7048* (2013.01); *A61K 45/06* (2013.01); *A61K 47/6937* (2017.08); *B82Y 5/00* (2013.01); *B82Y 40/00* (2013.01)

(58) Field of Classification Search
CPC ........ B82Y 5/00; B82Y 40/00; A61K 9/5192; A61K 47/6937; A61K 9/5146; A61K 31/12; A61K 31/135; A61K 31/192; A61K 31/337; A61K 31/7048; A61K 45/06
See application file for complete search history.

(56) References Cited

U.S. PATENT DOCUMENTS

| | | |
|---|---|---|
| 6,599,627 B2 | 7/2003 | Yeo et al. |
| 7,005,454 B2 | 2/2006 | Brocchini et al. |
| 8,137,699 B2 | 3/2012 | Johnson et al. |
| 8,586,098 B2 | 11/2013 | Lewis et al. |
| 8,685,538 B2 | 4/2014 | Torchilin et al. |
| 9,056,057 B2 | 6/2015 | Popov et al. |
| 2010/0330368 A1 | 12/2010 | Prud'Homme et al. |

FOREIGN PATENT DOCUMENTS

| | | | | |
|---|---|---|---|---|
| CN | 101836958 | * | 9/2010 | ............. A61K 47/38 |
| WO | 2004/091571 | | 10/2004 | |
| WO | 2005/105278 | | 11/2005 | |
| WO | WO-2011119262 A1 | * | 9/2011 | ................ A61J 1/00 |
| WO | 2015/200054 | | 12/2015 | |
| WO | 2017/112828 | | 6/2017 | |
| WO | 2017/161096 | | 9/2017 | |

OTHER PUBLICATIONS

Jingbin Huang, et al, Biodegradable Self-Assembled Nanoparticles of Poly(D,L-lactide-co-glycolide)/hyaluronic Acid Block Copolymers for Target Delivery of Docetaxel to Breast Cancer, 35 Biomat. 550 (Year: 2014).*
CN101836958 Machine Translation (Year: 2010).*
Jean-Louis Bourges, et al., "Ocular Drug Delivery Targeting the Retina and Retinal Pigment Epithelium Using Polylactide Nanoparticles", Investigative Ophthalmology & Visual Science, vol. 44, No. 8, Aug. 2003, pp. 3562-3569 (8 pages).
Fabienne Danhier, et al., "Paclitaxel-loaded PEGylated PLGA-based nanoparticles: In vitro and in vivo evaluation", Journal of Controlled Release, vol. 133, No. 1, 2009, pp. 11-17 (7 pages).
R. Dinarvand, et al., "Polylactide-co-glycolide nanoparticles for controlled delivery of anticancer agents", International Journal of Nanomedicine, vol. 6, 2011, pp. 877-895 (19 pages).
Jeffrey Hrkach, et al., "Preclinical Development and Clinical Translation of a PSMA-Targeted Docetaxel Nanoparticle with a Differentiated Pharmacological Profile", Science Translational Medicine, vol. 4, Issue 128 128ra39, Apr. 4, 2012, 12 pages.
Jingbin Huang, et al., "Biodegradable self-assembled nanoparticles of poly (D,L-lactide-coglycolide)/hyaluronic acid block copolymers for target delivery of docetaxel to breast cancer", Biomaterials, vol. 35, 2014, pp. 550-566 (17 pages).
Qianwen Li, et al., "A Review of the Structure, Preparation, and Application of NLCs, PNPs, and PLNs", Nanomaterials, vol. 7, No. 122, 2017, 25 pages.

(Continued)

*Primary Examiner* — Sean M Basquill
(74) *Attorney, Agent, or Firm* — Nixon & Vanderhye, P.C.

(57) ABSTRACT

A method of forming a core-shell polymer nanoparticle encapsulating an active agent is disclosed, including the use of a multi-solvent system in which to dissolve the active agent and a polymer prior to their precipitation using an antisolvent. The preferred use of an organic solvent system comprising two or more organic solvents allows for a high degree of control, as compared with the use of a single solvent, and enables the active agent to be precipitated more or less simultaneously with, or just prior to, the polymer.

14 Claims, 8 Drawing Sheets

(56) References Cited

OTHER PUBLICATIONS

Jennifer Logie, et al., "Innovative use of the taxol binding peptide overcomes key challenges of stable and high drug loading in polymeric nanomicelles", Chem. Commun., vol. 51, published Jun. 23, 2015, pp. 12000-12003 (4 pages).
K. Miladi, et al., "Particles From Preformed Polymers as Carriers for Drug Delivery", EXCLI Journal vol. 13, published Feb. 3, 2014, pp. 28-57 (30 pages).
Ros Azlinawati Ramli, et al., "Core-shell polymers: a review", RSC Advances, vol. 3, 2013, pp. 15543-15565 (24 pages).
Catarina Pinto Reis, et al., "Nanoencapsulation I. Methods for preparation of drug-loaded polymeric nanoparticles", Nanomedicine: Nanotechnology, Biology, and Medicine, vol. 2, 2006, pp. 8-21 (14 pages).
Sara Salatin, et al., "Development of a nanoprecipitation method for the entrapment of a very water soluble drug into Eudragit RL nanoparticles", Research in Pharmaceutical Sciences, vol. 12, No. 1, Feb. 2017, 14 pages.
Guoying Wang, et al., "Controlled preparation and antitumor efficacy of vitamin E TPGSfunctionalized PLGA nanoparticles for delivery of paclitaxel", International Journal of Pharmaceutics, vol. 446, 2013, pp. 24-33 (10 pages).
Q. Zhong, et al., "Polymeric perfluorocarbon nanoemulsions are ultrasound-activated wireless drug infusion catheters", Biomaterials, preprint posted online May 4, 2018, pp. 73-86 (34 pages).
International Search Report for PCT/AU2019/050557 dated Sep. 19, 2019, 4 pages.
Written Opinion of the ISA for PCT/AU2019/050557 dated Sep. 19, 2019, 5 pages.

* cited by examiner

US 11,766,409 B2

CORE-SHELL POLYMER NANOPARTICLE

This application is the U.S. national phase of International Application No. PCT/AU2019/050557 filed May 31, 2019 which designated the U.S. and claims priority to AU Patent Application No. 2018901933 filed May 31, 2018, the entire contents of each of which are hereby incorporated by reference.

FIELD OF THE INVENTION

The invention relates to the field of polymer particles as delivery agents. More particularly, this invention relates to a method of synthesising a core-shell polymer nanoparticle, the core-shell polymer nanoparticle thereby produced and its use in delivery of an active agent.

BACKGROUND TO THE INVENTION

Any reference to background art herein is not to be construed as an admission that such art constitutes common general knowledge in Australia or elsewhere.

Core-shell polymer nanoparticles may be considered as a polymeric nanoparticle with at least two defined regions and with one region, the core, more or less encapsulated by another region, the shell. They can provide for improved properties and ensuing benefits not attainable from either component individually.

In biomedical applications the core region may be an active agent to be delivered to a patient. In such applications, core-shell polymer nanoparticles can be particularly useful in formulating poorly soluble drugs for improved bioavailability, safety, tolerability and efficacy. Approximately 40% of approved drugs and 90% of pipeline drugs exhibit poor water solubility, and so there is a significant need for new systems, such as core-shell polymer nanoparticles, which can deliver hydrophobic drugs to the appropriate biological sites at adequate therapeutic levels.

One of the major challenges hindering the practical application of most nanoparticle delivery systems is the low drug loading typically achieved. Among many nano-systems, drug loading is usually below 10% and polymeric nanoparticles having drug loading lower than 5% or even less than 1% are not uncommon.

The drug loading is strongly impacted by the method of formation of the core-shell polymer nanoparticle. A variety of approaches have been tested in the art with emulsion polymerisation, dispersion polymerisation and precipitation polymerisation being three of the most common.

Nanoprecipitation, is perhaps the most straightforward method for preparing drug-loaded core-shell polymer nanoparticles. Typically, a polymer and a drug are dissolved in a solvent, and then this solution is rapidly added to an 'antisolvent', for example water, to form the drug-loaded core-shell polymer nanoparticles. Fast mixing, to thereby encourage a short precipitation time, is suitable for making uniform and monodispersed nanoparticles. The drug loading efficiency (DLE: drug amount/Core-shell polymer nanoparticles amount) of the core-shell polymer nanoparticles using such an approach is generally low, with most systems offering under 5% DLE. This is mainly due to the significant difference in the precipitation time of the drug and the polymer which means that, if the drug precipitates faster than the polymer, the precipitated drug will form larger aggregate structures leading to the subsequent formation of polymeric nanoparticles with very low drug loading. Clearly if the polymer precipitates prior to the drug then drug loading will be extremely low.

It would be useful to provide core-shell polymer nanoparticles formed in a controlled manner to optimise drug loading for the delivery of active agents, such as drug molecules, which ameliorates, overcomes or circumvents one or more of these problems.

SUMMARY OF INVENTION

According to a first aspect of the invention, there is provided a method of forming a core-shell polymer nanoparticle comprising an active agent including the steps of:
  (a) dissolving a polymer and an active agent in a solvent system, the solvent system comprising at least two organic solvents, to thereby form an active solution;
  (b) mixing the active solution with at least one antisolvent to precipitate the active agent and the polymer; and
  (c) allowing the precipitated polymer and active agent to form a core-shell polymer nanoparticle comprising the active agent.

A second aspect of the invention resides in a core-shell polymer nanoparticle comprising an active agent when produced by the method of the first aspect.

A third aspect of the invention resides in a method of delivering an active agent to a subject by administering a core-shell polymer nanoparticle of the second aspect to the subject.

A fourth aspect of the invention resides in a method of preventing or treating a disease or condition including the step of administering a therapeutically effective amount of a core-shell polymer nanoparticle of the second aspect to a subject in need thereof.

A fifth aspect of the invention resides in the use of a core-shell polymer nanoparticle of the second aspect in the manufacture of a medicament for the treatment of a disease or condition.

A sixth aspect of the invention resides in a core-shell polymer nanoparticle comprising an active agent for use in preventing or treating a disease or condition.

The various features and embodiments of the present invention, referred to in individual aspects above apply, as appropriate, to other aspects, mutatis mutandis. Consequently, features specified in one aspect may be combined with features specified in other aspects, as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein.

DETAILED DESCRIPTION

Figure 1:
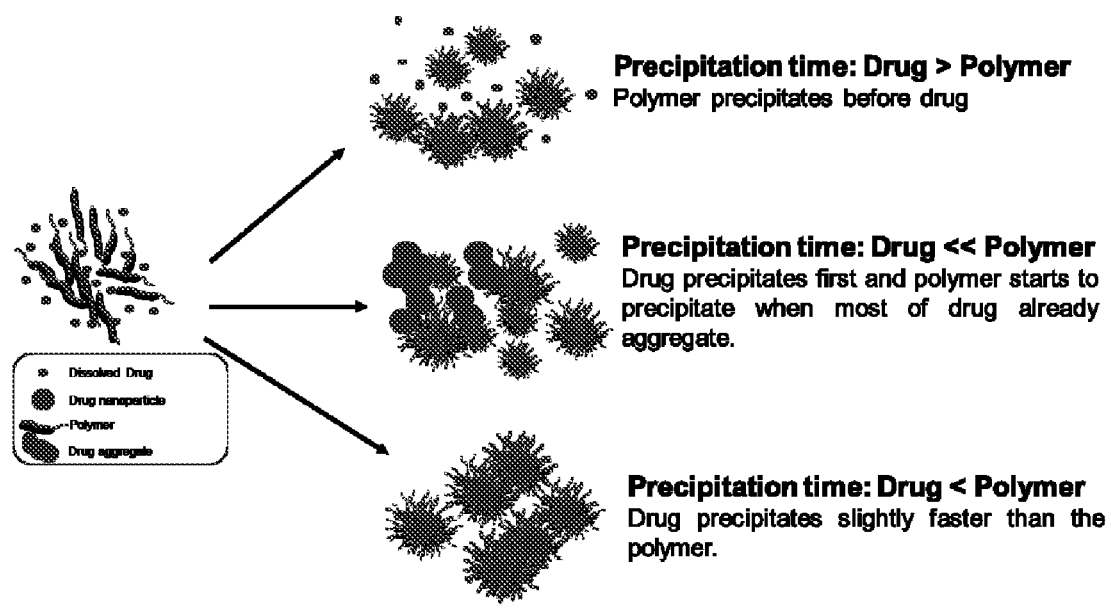
FIG. 1 is a schematic indicating variations of core-shell polymer nanoparticle loading outcomes with timing of precipitation of the polymer and active agent (in this instance a drug molecule)

The present invention is predicated, at least in part, on the finding that the timing of the precipitation of an active agent and polymer from solution, following contact with an antisolvent, can be controlled by the use of an organic solvent system comprising two or more organic solvents. This allows for a high degree of control, as compared with the use of a single solvent, and enables the active agent to be precipitated more or less simultaneously with, or preferably just prior to, precipitation of the polymer. This is a preferred sequence as the precipitated active agent is available for encapsulation but has not been precipitated for a sufficient amount of time to form larger drug-aggregate structures, which can be detrimental to the formation of highly loaded core-shell polymer nanoparticles.

Such an approach provides greater flexibility in terms of the choice of active agent and polymeric shell. Whereas a typical approach of precipitating the active and polymer from a single solvent likely means the screening of many polymers to ensure a similar precipitation time as compared with the active, with ensuing limitations on the nature of the active-polymer combination, the present approach allows for optimal matching of an active with a polymer with the desired physical properties. The matching of their respective precipitation times to be close to one another can then be addressed simply by manipulation of the solvent system used to dissolve both active agent and polymer to form what is termed herein the 'active solution'.

In this patent specification, adjectives such as first and second, left and right, front and back, top and bottom, etc., are used solely to define one element or method step from another element or method step without necessarily requiring a specific relative position or sequence that is described by the adjectives unless such is clear from the context.

Unless defined otherwise, all technical and scientific terms used herein have the same meaning as would be commonly understood by those of ordinary skill in the art to which this invention belongs.

As used herein, the term "core-shell polymer nanoparticle" refers generally to a polymeric particle having an active agent substantially surrounded with at least one outer polymeric layer. The active agent may be incorporated within a polymeric matrix within the particle. In certain embodiments the particle size/diameter of the core-shell polymer nanoparticle may be between 15 to 2000 nm, more preferably between about 20 to 1000 nm, even more preferably between about 25 to 500 nm. In preferred embodiments, the core-shell polymer nanoparticles will substantially fall within the 30 to 200 nm size range. In embodiments, the active agent will be in nanoparticulate form. In certain embodiments, the active agent will be completely encapsulated by the polymer. In embodiments, the core-shell polymer nanoparticle produced according to the method of the invention may have a polydispersity index (PDI) of less than 0.2.

The term "active agent" will be used herein largely to refer to therapeutic agents and particularly to small molecule therapeutic drugs. It will be appreciated, however, that any compound which can be precipitated to form nano-sized particles capable of being encapsulated by self-assembly of the precipitated polymer may be suitable for use as the active agent. This means that industrial chemicals such as antioxidants, anti-fouling agents and the like, which may be added to paints and other industrial formulations, may be used as the active agent and such agents and their encapsulation using the present method are explicitly considered within the scope of the present invention.

As used herein, the word "mixing" may refer to any means of causing agitation, perturbation, blending or other dynamic movement of the active solution with the antisolvent during the mixing leading to precipitation. Stirring, pipette mixing, injection, continuous flow techniques, micromixing and mechanical mixing are preferred means of agitating the fluids although, sonication, shaking and other means may be acceptable.

In a first aspect of the invention, there is provided a method of forming a core-shell polymer nanoparticle comprising an active agent including the steps of:
   (a) dissolving a polymer and an active agent in a solvent system, the solvent system comprising at least two organic solvents, to thereby form an active solution;
   (b) mixing the active solution with at least one antisolvent to precipitate the active agent and the polymer; and
   (c) allowing the precipitated polymer and active agent to form a core-shell polymer nanoparticle comprising the active agent.

In embodiments, the polymer may be a natural or synthetic biocompatible polymer.

The natural polymer may be a resin.

In one embodiment, the resin may be shellac or rosin.

In embodiments, the polymer may be a block copolymer and/or enteric coating polymer.

In certain embodiments, the polymer may be an amphiphilic block copolymer.

In further embodiments, the polymer may be an amphiphilic di-block copolymer.

In embodiments, the polymer is not water soluble.

The natural polymer may comprise polyhydroxy acids and/or esters and/or polyesters thereof.

The polymer may be formed from monomers selected from the group consisting of lactic acids, glycolic acids, lactide, glycols, alkene oxides, acrylates, hydroxyalkanoates, terephthalates, and succinates.

The polymer may be or may comprise a polymer selected from the group consisting of poly(lactide-co-glycolide)-b-poly(ethylene glycol), shellac, PLGA, poly(D,L-lactide)-b-poly(ethylene glycol), poly(L-lactide)-b-poly(ethylene glycol), poly(caprolactone)-b-Poly(ethylene glycol), poly(acrylic acid), poly(ethylene oxide), poly(ethylene glycol), poly(methyl methacrylate), polystyrene, poly(pyridyldisulfide ethylmethacrylate), poly(N-isopropylacrylamide), poly(methacrylic acid), poly(lactic-co-glycolic acid), polylactic acid, polyglycolic acid, polycaprolactone, polylysine, polyglutamic acid, polyarginine, polylysine, polyhistidine, polyornithine, polyethyleneimine, polypropyleneimine, poly(allylamine), polystyrene-maleic acid, gelatin, polycrotonic acid, polyaspartic acid, hyaluronic acid, alginic acid, polystyrene sulfonate, carrageenan, poly(methylene-co-guanidine), polyphosphoric acid, pamidronic acid, polycarbophil, poly(methylvinyl ether-co-maleic anhydride), shellac, agar, pectin, polyvinyl acetate phthalate, guar gum, polyethylene glycol, polydextrose, poly-L lactide (PLLA), poly-DL-lactide (PDLLA), L-lactide/DL-lactide copolymers, lactide/tetramethyl-glycolide copolymers, poly-valerolacton (PVL), poly-hydroxy butyrate (PHB), poly vinyl alcohol (PVA) poly-hydroxyvalerate (PHV), polyvinylpyrrolidone (PVP), pollulan, hypromellose acetate succinate, hypromellose phthalate, Eudragit®L 100-55 and blends thereof.

In certain embodiments, the polymer may be selected from the group consisting of poly(lactic-co-glycolic acid) (PLGA), poly(lactic acid) (PLA), poly(lactic-co-ethylene glycol) (PLA-PEG), poly(lactic-co-glycolic acid)ethylene glycol (PLGA-PEG) and shellac. References to poly(lactic acid) within a homopolymer or copolymer context include both D- and L-forms either separately or within the one polymer.

In embodiments, the polymer dissolved in the active solution may be 2 or more individual polymers selected from any of those classes and examples discussed above. The polymers may be in any ratio of rom 10:1 to 1:10 including 6:1 to 1:6. For example, in an active solvent comprising PLGA-PEG and a second polymer then the ratio may be from 6:1 PLGA-PEG:second polymer to 1:6 PLGA-PEG:second polymer. The second polymer may be selected from those previously discussed and including, for example, shellac, PLGA, PLLA, PLA and PLLA-PEG.

In such embodiments, the method may include the step of precipitating the individual polymers from the active solution sequentially. This may allow the nanoparticle to form with the first polymer precipitating around the active agent and the second, or further, polymer subsequently precipitating to form a second polymeric layer around the shell formed by the first polymer.

In certain embodiments, the method may include the step of selecting a molecular weight range of the polymer. Many commercially available polymers are provided in molecular weight ranges. The molecular weight of the polymer may affect its precipitation time within the solvent system. For example, in certain solvents PLGA with a lower molecular weight has a longer precipitation time. Selecting the molecular weight range of the polymer can therefore provide a further layer of control in the present approach.

In one embodiment, the active agent may be selected from the group consisting of a small molecule drug, a chemotherapy drug, a radiotherapy drug, a photodynamic therapy drug, an anesthetic, an anti-inflammatory, and an imaging agent.

In particular embodiments, the active agent may be selected from the group consisting of an anti-infective, antimalarial, antiviral, antibiotic, antifungal, antioxidant, antiprotozoal, antineoplastic, cardiovascular agent, antihypertensive, analgesic, anticoagulant, antidepressant, antiarthritic, antipsychotic, neuroprotective, radiologic, respiratory agent, anti-cancer, anti-migraine, enzyme inhibitor, cancer growth blocker and antipyretic.

In embodiments, the active agent may be selected from taxol (paclitaxel), taxol derivatives including docetaxel, doxorubicin, bulleyaconitine A, amphotericin B, scutellarin, quercetin, vemurafenib, silibinin, oleanolic acid, betulinic acid, honokiol, camptothecin, camptothecin derivatives, curcumin and curcumin derivatives, ibuprofen and ketamine.

It will be appreciated that the active agent, when it is a therapeutic molecule, may be a pharmaceutically acceptable prodrug, salt or ester or isomer or derivative of the biologically active molecule.

In certain embodiments, the active agent is a hydrophobic active agent. Put another way, in certain embodiments, the active agent is non-polar.

Therefore, in embodiments, the active agent will have poor water solubility. The level of water solubility can be tested by well-known means of finding out the amount of the substance which can dissolve in water at a given temperature. In one embodiment, 'poor water solubility' may be considered to be attributed to any substance which requires greater than 50, preferably greater than 100, more preferably greater than 500, even more preferably greater than 1000, such as greater than 5000, mass parts of water to dissolve one part of said substance.

In certain embodiments, the active agent has a molecular mass of less than 5,000 Daltons, or less than 3,000 Daltons or less than 2,000 Daltons, or less than 1000 Daltons, and in another embodiment, the active agent has a molecular mass of less than 950 or 850 Daltons. Any of these values may be coupled with a lower molecular mass value of 20, 30 or 50 Daltons to form a molecular mass range such as 20 to 5,000, 20 to 3,000, 20 to 2,000, 20 to 1000, 20 to 950 or 20 to 850 Daltons.

The w/w ratio of the active agent to the polymer (being the total polymer content) in the active solution may be between 5:1 to 1:5. Suitably, the w/w ratio of the active agent to the polymer is between 3:1 to 1:3 including 2:1 to 1:2 and is preferably about 1:1.

It will be appreciated that, in certain embodiments, the active agent may comprise two or more active agents including 2, 3 or 4 active agents within the nanoparticle. This may be useful in a multi-drug administration treatment.

In embodiments, the solvent system is less polar than the antisolvent. That is, the solvent system will have an overall lower dielectric constant value than the antisolvent. Freely available tables or scales of dielectric values may be used or the dielectric constant measured using standard approaches well-known in the art.

It will be understood that, as the solvent system is formed from at least two organic solvents, the solvent system does not comprise water or another non-organic solvent. That is, the solvent system comprises only organic solvents being those which are carbon-based i.e. which are composed of organic compounds or volatile organic compounds.

It will also be understood that "at least two organic solvents" means two or more organic solvents which are all different, one from the other(s).

In embodiments, each solvent forming the solvent system is of a different solvent type or class. The different solvent type or class may be determined by reference to, for example, the functional group displayed. For example, hydroxyl for alcohols. Therefore, if one solvent of the solvent system is an alcohol then it is preferred that the other solvents are not alcohols or at least one other is not.

Suitably, all organic solvents in the solvent system are liquid at atmospheric pressure (such as mean sea level pressure) and room temperature (such as about 18° C. to 25° C.).

Therefore, in one embodiment, the solvent system does not include carbon dioxide, liquefied or otherwise.

In embodiments, the solvent system may comprise three or more organic solvents.

The solvents, preferably organic solvents, forming the solvent system may be selected from the group consisting of a formamide, a sulfoxide, an alcohol, an aliphatic ether, a cyclic ether, an ester, an alkane, a haloalkane, an amine, a ketone and an aromatic.

In certain embodiments, each of the solvents, preferably organic solvents, forming the solvent system may be selected from the group consisting of DMSO, DMF, methanol, ethanol, and acetone.

In one embodiment, at least one of the organic solvents forming the solvent system is selected from DMSO and DMF. If the solvent system comprises only two organic solvents and one solvent is neither DMSO or DMF then that organic solvent is preferably an alcohol. In preferred embodiments, that alcohol may be methanol or, more preferably, ethanol.

In certain embodiments, the majority of the solvent system is made up of DMSO and DMF. For example, between 51% to 90% (v/v) of the solvent system may be made up of DMSO and DMF, including 55% to 85% (v/v).

In certain embodiments, DMSO may form at least 20% (v/v) of the solvent system. Preferably, DMSO forms at least 25% (v/v) of the solvent system.

In embodiments, DMSO may form between 20% to 70% (v/v) of the solvent system, including between 20% to 60% (v/v).

Where the solvent system comprises three organic solvents and the majority of the solvent system is made up of DMSO and DMF then the third organic solvent may be selected from methanol and ethanol.

When the solvent system comprises DMF, DMSO and ethanol then they may be present in the following v/v ranges: between 20% to 45% DMF, between 20% to 60% DMSO and between 10% to 50% ethanol. Suitably, the ranges may be between 25% to 35% DMF, between 25% to 55% DMSO and between 15% to 45% ethanol.

The development of this multi-solvent approach, in forming the active solvent in which both the active agent and polymer are dissolved (within the solvent system) prior to contact with the antisolvent, is a key difference over the approaches of the prior art and provides for the advantages discussed herein.

To achieve drug-encapsulated core-shell polymer nanoparticles, the aim is generally to match the precipitation time of the drug and the polymer, although ideally the present inventors have found that the drug should precipitate slightly earlier than the polymer, so that before the small drug particles assemble into larger aggregates they can be stabilized by the formation of the self-assembled polymer layer on and around the drug particles. This comparison of the effects of varying relative precipitation rates is indicated schematically in FIG. 1. Due to the intrinsic variation in properties of the drug and the polymer, their precipitation times are typically very different. It is difficult to adjust their precipitation times when using a single solvent approach to form the active solution, as is standard in the prior art, but the present inventors have found it can be achieved by using a plurality of organic solvents and adjusting their relative ratios to account for the differing active agent (drug) and polymer properties.

As discussed, traditional precipitation methods are based on fast precipitation of both active and polymer by adding a relatively small volume of the active solution containing both active and polymer to a large volume of antisolvent, thereby rapidly precipitating to form drug-encapsulated nanoparticles, but with very low drug loading. The present multi-solvent approach is to add anti-solvent to the multi-solvent solution containing both active and polymer, which allows the formation of drug nanoparticles followed by the precipitation of polymer forming the polymer shell. This multi-organic solvent approach can make it possible to optimise the precipitation time for a wide variety of combinations of polymer and drug providing for a controlled precipitation approach.

The provision of this level of fine control is particularly useful when forming core-shell polymer nanoparticles with certain active agents. For example, some nano-sized drugs, such as curcumin, may be stable for up to 48 hours. However, some nano-sized drugs, such as paclitaxel and ibuprofen, are very unstable, once formed, and will aggregate in less than a second. For the drugs which can form stable nano-sized drug particles, the screening of the parameters, as described herein, for adjusting the drug and polymer's precipitation time is somewhat flexible and a range of conditions can be found under which the polymer can be precipitated later than the formation of the nano-sized drug particles with the additional consideration that the longer the precipitation time is for the polymer then the larger the size of the nanoparticles obtained. Therefore, curcumin may have several working formulations, with mainly the size of the formed nanoparticles being the only variation in output. However, for drugs such as paclitaxel, the parameters (the solvent system and pH) are stricter as the polymer needs to cover the formed nano-sized paclitaxel particles very quickly to prevent them from aggregating.

Therefore, in one embodiment, the method includes the step of causing the active agent to substantially precipitate prior to the polymer.

In some embodiments, the method may include the step of causing the active agent to substantially precipitate immediately prior to the polymer. The term "immediately prior' in this context may mean the polymer will precipitate, following precipitation of the active agent, within less than 30 seconds, or less than 20 seconds, or less than 10 seconds, or less than 5 seconds, or less than 2 seconds or within about 1 second.

Due to the efficiency of nanoparticle formation, it is a further advantage of the present method that a separate step of stabilising the core-shell polymer nanoparticle is not required.

Therefore, in one embodiment, the method does not include addition of a separate cross-linking agent to stabilise the particle.

In one embodiment, the method does not include addition of a separate surfactant to stabilise the particle.

Nonetheless, the core-shell polymer nanoparticles formed by the present method are highly stable over the long term. They have demonstrated other desirable properties such a PDI of less than 0.2 thereby providing uniform particle sizes which can be tailored effectively.

In embodiments, the method does not include the addition of a metal or metal salt, which is not already present in the antisolvent to form a buffer solution, to the solvent system, active solution or antisolvent.

In embodiments, the antisolvent is a polar solvent.

Preferably, the antisolvent is a polar non-organic compound.

In certain embodiments, the antisolvent is an aqueous solution.

The antisolvent may have a pH of between about 3 to about 9, including between about 4 to about 8.

The antisolvent may comprise water or an aqueous buffer solution.

In one embodiment, the aqueous buffer solution is an acidic buffer solution. In an embodiment, the pH of the aqueous buffer solution is between 3 to 6, or between 3 to 5, preferably 4 to 5.

The aqueous buffer solution may be a solution comprising one or more of potassium chloride, sodium chloride, disodium hydrogen phosphate and potassium dihydrogen phosphate.

Preferably, the aqueous buffer solution is a phosphate-buffered saline (PBS) solution.

In an embodiment, the at least one antisolvent is a single solvent or solution. That is, the antisolvent comprises a single solvent which may, as described above, comprise various solute(s) to form a solution.

In embodiments, the ratio of antisolvent to solvent system is between about 5:1 to about 50:1, preferably between about 10:1 to about 40:1, more preferably between about 10:1 to about 30:1, including about 10:1 to about 20:1.

The mixing of the antisolvent and active solution may be accomplished by a number of means. As discussed above, it is one advantage of the present approach that flash mixing or other complex and expensive mixing approaches may not be necessary due to the focus on control of the precipitation time instead of focus on ultra-efficient mixing to adapt for no or minimal control of precipitation.

That is, the present multisolvent system approach is almost independent of the mixing time or mixing type, because it changes the intrinsic solubility or precipitation time of the active agent and polymer, so they can precipitate out in a sequential manner. This is a distinct advantage from other approaches where the mixing time, velocity or technique can be crucial and outcomes thereby highly variable.

In embodiments, the antisolvent may be added to the active solution in more than one portion, interspersed with mixing. In one embodiment, the antisolvent volume may be added in two or three separate portions. In a further embodiment, the antisolvent volume may be added by a continuous flow.

In one embodiment, the active solution and the antisolvent are mixed by mechanical mixing including stirring or pipette mixing, injection, confined impinging jet mixing, vortex mixing, multi-injection vortex mixing, microfluidic mixing or continuous flow mixing.

In one embodiment, the method includes the step of adjusting the pH of the solvent system or the antisolvent to be either acidic or alkaline.

A second aspect of the invention resides in a core-shell polymer nanoparticle comprising an active agent when produced by the method of the first aspect.

Preferably, the particle diameter is between 15 to 2000 nm, more preferably between about 20 to 1000 nm, even more preferably between about 25 to 500 nm.

In embodiments, the drug loading efficiency within the core-shell polymer nanoparticles is greater than 10%, or greater than 20%, or greater than 30%, or greater than 40%, or greater than 50%.

It is an advantage of the present method that the control of precipitation leads to an optimised sequence of active agent precipitation followed closely by polymer precipitation, prior to formation of any significant amount of aggregation of the active agent, such that the active agent is immediately ready and of an optimal nano-size for efficient polymer encapsulation.

The core-shell polymer nanoparticle comprising an active agent of the second aspect may be formed according to, or may have the properties of, the method or output as described in any statements for the first aspect as if they were reproduced herein in relation to the second aspect.

A third aspect of the invention resides in a method of delivering an active agent to a subject by administering a core-shell polymer nanoparticle of the second aspect to the subject.

According to a fourth aspect of the invention resides in a method of preventing or treating a disease or condition including the step of administering a therapeutically effective amount of a core-shell polymer nanoparticle of the second aspect to a subject in need thereof.

A fifth aspect of the invention resides in the use of a core-shell polymer nanoparticle of the second aspect in the manufacture of a medicament for the treatment of a disease or condition.

A sixth aspect of the invention resides in a core-shell polymer nanoparticle comprising an active agent for use in preventing or treating a disease or condition.

The core-shell polymer nanoparticle comprising an active agent for any of the third to sixth aspects may be that of the second aspect and may be formed, or may be as defined, as described in any embodiment of the first aspect or any combination of such aspects.

The use of the third aspect may be in relation to active delivery for theranostic applications. In such applications the active agent may be or comprise liposomes, dendrimers, polymeric nanoparticles, imaging agents, metallic nanoparticles, quantum dots and carbon nanotubes. The applications may be, for example, pharmacogenetics, proteomics and biomarker profiling as well as diagnostics generally.

It will be appreciated by those skilled in the art that any composition formulated for the purposes of the third, fourth, fifth or sixth aspect may be formulated using any number or combination of excipient materials. These excipient materials may be included in a formulation for any number of reasons well known to those skilled in the art including, but not limited to, providing a stable formulation, improving flowability, adjusting pH, allowing easy reconstitution, stabilising the particles, minimising adverse toxicological responses, improving manufacturability, increasing stability or lifetime or allowing easier administration, storage or transportation. Such excipient materials are widely known in the art and are readily available through commonly used commercial channels.

By way of example only, excipients that could be used to formulate the present core-shell polymer nanoparticles into a composition to deliver to a subject may include, but are not limited to, acetone, alcohol, anhydrous lactose, castor oil, cellulose acetate phthalate, dextrose, D-fructose, D-mannose, FD&C Yellow #6 aluminium lake dye, fetal bovine serum, human serum albumin, magnesium stearate, microcrystalline cellulose, plasdone C, polacrilin potassium, sodium bicarbonate, sucrose, aluminium hydroxide, amino acids, benzethonium chloride, formaldehyde, inorganic salts and sugars, vitamins, asparagine, citric acid, lactose, glycerin, iron ammonium citrate, magnesium sulfate, potassium phosphate, aluminium phosphate, formaldehyde, glutaraldehyde, 2-phenoxyethanol, glutaraldehyde, polysorbate 80, aluminium potassium sulfate, ammonium sulfate, bovine extract, gelatin, peptone, sodium phosphate, thimerosal, calf serum, glutaraldehyde, lactalbumin hydrolysate, neomycin sulfate, polymyxin B, lactalbumin hydrolysate, yeast extract, MRC-5 cellular protein, neomycin, polymyxin B sulphate, aluminium hydroxyphosphate sulphate, hemin chloride, mineral salts, nicotinamide adenine dinucleotide, potassium aluminium sulfate, sodium borate, soy peptone, phosphate buffers, polsorbate 20, sodium borate, lipids, sodium dihydrogen phosphate dehydrate, carbohydrates, L-histidine, Beta-propiolactone, calcium chloride, dibasic sodium phosphate, egg protein, monobasic potassium phosphate, monobasic sodium phosphate, polymyxin B, potassium chloride, sodium taurodeoxychoalate, gentamicin sulfate, hydrocortisone, octoxynol-10, a-tocopheryl hydrogen succinate, sodium deoxycholate, ovalbumin, nonylphenol ethoxylate, octylphenol ethoxylate (Triton X-100), arginine, dibasic potassium phosphate, egg protein, ethylene diamine tetraacetic acid, gentamicin sulfate, hydrolyzed porcine gelatin, monobasic potassium phosphate monosodium glutamate, protamine sulfate, sodium metabisulphite, phenol, casamino acid, sodium citrate, sodium phosphate monobasic monohydrate, sodium hydroxide, calcium carbonate, dextran, sorbitol, trehalose, sugar alcohols, polysaccharides, glucosamine, mannitol, polymers and xanthan.

An appropriate dosage may be simply determined by calculating the loading of the active agent within the core-shell polymer nanoparticle and then using an amount of said loaded nanoparticle which is broadly equivalent to the dosage of the free active agent which would typically be given to a patient.

As discussed previously, more than one active agent may be coated within a core-shell polymer nanoparticle formulation either at the time of formation (by having the actives within solution at the same time and assuming a similar solubility profile) or separate formulations of different active agents may be made up and then mixed. The dual active formulations may then be used in a co-treatment regime. It will be appreciated that any treatment regime can be mimicked by the present approach as it simply requires the forming of the core-shell polymer nanoparticles encapsulating the active agent(s) of interest and then treatment can be approached in a broadly equivalent manner to that using the free actives.

As used herein, the terms "subject" or "individual" or "patient" may refer to any subject, particularly a vertebrate subject, and even more particularly a mammalian subject, for whom therapy or prophylaxis is desired. Suitable vertebrate animals include, but are not restricted to, primates, avians, livestock animals (e.g., sheep, cows, horses, donkeys, pigs, fish), laboratory test animals (e.g., rabbits, mice, rats, guinea pigs, hamsters), companion animals (e.g., cats, dogs) and captive wild animals (e.g., foxes, deer, dingoes). A preferred subject is a human.

The disease or condition may be any one or more of those treated by the active agents listed in relation to the first aspect. Such conditions may include, pain, fever, cancer, arthritis, and inflammation.

In embodiments, the disease or condition being treated or prevented may be selected from the group consisting of infections (bacterial and/or viral and/or fungal and/or protozoal), malaria, antioxidant, antiprotozoal, neoplastic, cardiovascular, hypertension, pain, blood coagulation, depression, arthritis, psychosis, respiratory, migraine, fever and inflammation.

EXPERIMENTAL

General Approach

It will be appreciated that the present method requires a degree of optimisation of the solvent system for each drug/polymer combination. A distinct advantage, however, is that this can be accomplished in a reliable and methodical manner, without undue burden or the need for inventive skill, as will be described below.

To find the best combination of different solvents, a simple screening method was developed. Curcumin-loaded shellac core-shell polymer nanoparticles were employed as an example but the principle can be applied to any combination of active agent and polymer.

1. Determining the Optimal Curcumin Concentration to Form Uniform Nanocurcumin:
1) Curcumin was dissolved in DMF at different concentrations (0.1, 1, 2, 4, 6, 8, 10, 15, 20, 30, and 60 mg/ml).
2) 3800 μL water was added into the 200 μL curcumin-DMF solutions with pipette mixing. The nanosuspension was then characterised using Dynamic Light Scattering (DLS) and the desired concentration of solution selected based upon which gave uniform, relatively small nanoparticles and lower PdI value.
3) The results indicated that 3~10 mg/ml was an optimal curcumin in DMF concentration with a nanoparticle size of around 50 nm and PDI less than 0.1, being observed.
4) To obtain the precipitation curve of curcumin in DMF, 20 μL water was added into the 180 μL curcumin-DMF (3 mg/ml) solutions with pipette mixing. The Derived Count Rates (DCR) result from Dynamic Light Scattering was measured. Then, every time 20 μL water was added and DCR results were recorded. When 300 μL water (i.e., water/solvent volume ratio=1.67:1) was added, the curcumin just started to precipitate (3% precipitated). The minimum water/solvent ratio was 2.2:1 (v/v) to make most of the curcumin (3 mg/ml) precipitate, when the relative nanoparticle amount increased to the highest point (relative nanoparticle amount=DCR×volume).

2. Determining the Precipitation Volume of Shellac:
1) The polymer shellac, with a concentration of 3~10 mg/ml (to provide a 1:1 ratio with curcumin), was dissolved in DMF.
2) Then water was added into the 180 μL shellac-DMF (3 mg/ml) solutions step-by-step (20 μL water each time) with pipette mixing. The Derived Count Rates (DCR) results from Dynamic Light Scattering were recorded.
3) The minimum water/solvent ratio to make 84% of the shellac (3 mg/ml) precipitate was only 1.67:1 (v/v), at this water/solvent ratio, only 3% curcumin precipitated. This is one of the reasons why traditional nanoprecipitation methods have a very low drug loading efficiency (less than 5%) using a single solvent (DMF only) system because, when most of the core-shell polymer nanoparticles are forming, the drug hasn't started to precipitate as most of the drug is still soluble.

3. Adjusting the Precipitation Time of Shellac:
1) The solubility of shellac in DMF and ethanol is similar, and it is higher in DMSO. Therefore, by adding DMSO to DMF it is possible to slow down the precipitation of shellac, or one can increase the water/solvent ratio. Also, replacing water with PBS can slow down the precipitation of shellac, because shellac has higher solubility under alkaline conditions.
2) A series of shellac-DMF-DMSO solutions with 3 mg/ml shellac and different DMSO ratios (5%, 10%, 15%, 20%, 25%, 30%, 35%, 40%, 45%, and 50%) were prepared.
3) PBS was added into the 180 μL shellac-DMF-DMSO (3 mg/ml) solutions with different DMSO ratios step-by-step (20 μL PBS each time) with pipette mixing respectively. The Derived Count Rates (DCR) results from Dynamic Light Scattering were recorded. The precipitation curves (X axis: water/solvent ratio; Y axis:relative nanoparticle amount=DCR×volume) of shellac-DMF-DMSO (3 mg/ml) solutions with different DMSO ratios were made.
4) The precipitation curve of the 40% DMSO had the lowest slope which implied the slowest precipitation of shellac.

4. Adjusting the Precipitation Time of Curcumin:
1) To achieve stable higher drug loading nanoparticles, it is beneficial to precipitate the nano-drug first, then the polymer coats the nano-drug particles, which allows for the long-term stability of drug-loaded nanoparticles.
2) This means it was preferable to reduce curcumin's precipitation time (increase the slope of curcumin's precipitation curve). Because curcumin's solubility in ethanol is much lower than in DMF and DMSO, a series of curcumin-ethanol-DMF-DMSO$_{40\%}$ (the volume ratio of DMSO in the three-solvent system was kept at 40%) solutions were prepared with 3 mg/ml curcumin concentration and different ethanol ratios (5%, 10%, 15%, 20%, 25%, 30%, 35%, 40%, 45%, and 50%) by keeping the same ratio of DMSO to the total solvent mixture (4:10). PBS was added into the 180 μL curcumin-ethanol-DMF-DMSO40% (3 mg/ml) solutions with different ethanol ratios continually (20 μL PBS each time) with pipette mixing respectively. The Derived Count Rates (DCR) results from Dynamic Light Scattering were recorded continually.
3) The minimum PBS/solvent ratio was 0.89:1 (v/v) for the 30% ethanol formulation to make most of the curcumin precipitate. The minimum PBS/solvent ratio is 2.22:1 (v/v) for most of shellac precipitate, and the slope of curcumin's precipitation curve was higher than the slope of shellac which allows sequential precipitation and coating to form stable core-shell polymer nanoparticles.

5. Optimising the Water/Solvent Ratio for the Final Solvent Formulation:
1) Based on the above 4 steps, an optimal formulation of ethanol:DMF:DMSO of 3:3:4 (v/v/v) was determined for 3 mg/ml curcumin and 3 mg/mL shellac.
2) Curcumin and shellac (3 mg/mL for both) were dissolved in this solvent system, then PBS was added with pipette mixing. The size and PdI results from Dynamic Light Scattering were recorded.
3) Different PBS/solvent ratios were tested including 2:1, 5:1, 10:1, 20:1, 30:1 and 40:1 (v/v).
4) Different ways of adding the PBS were also tested, including adding all PBS at one time or in separate portions with mixing.
5) The optimal PBS/solvent ratio was found to be 10:1~20:1 which provides smaller nanoparticles (<100 nm) and the optimal way to add the PBS was found to be adding PBS by twosteps. Adding PBS to 50% of the total volume with mixing, then adding the remaining subsequently with further mixing.

In conclusion, following this five-step process, a method for achieving a drug loading of 50% of curcumin in shellac nanoparticles was developed. The solvent formulation developed was Ethanol:DMF:DMSO=3:3:4 (v/v/v) with 3 mg/ml curcumin and 3 mg/ml shellac concentration. Adding 9 times PBS (volume) with mixing firstly to achieve the volume ratio of 10:1, then continuing adding the remaining PBS in the same manner, to have the final volume ratio of 20:1.

6. Encapsulation of Other Drugs with PLGA-PEG or Shellac:

Curcumin is very hydrophobic (0.6 μg/mL solubility in water). Based on this formulation and the method developed, the ratio can be adjusted slightly to achieve high drug loading nanoparticles. A number of different kinds of drugs were subsequently tested and the results show that even with varying the active agent and polymer, it is still possible, following the approach outlined, to achieve stable high drug loading core-shell polymer nanoparticles. Table 1 below indicates the results of such a series of tests.

Figure 4:
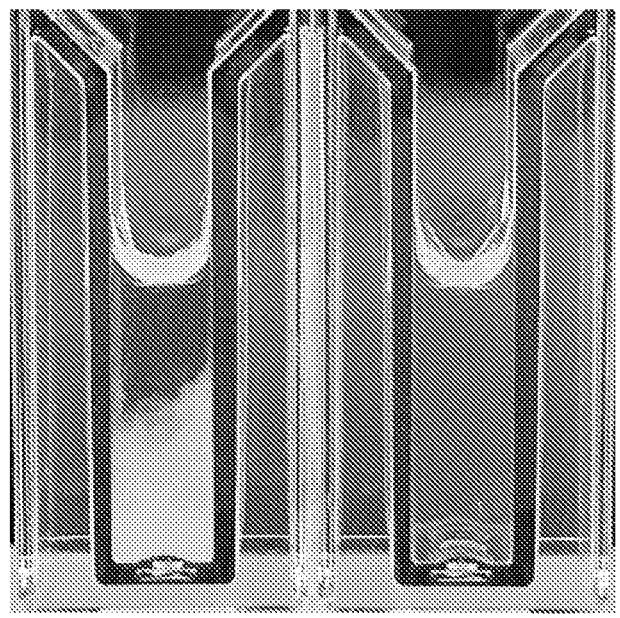
FIG. 4 is a photo of free Amphotericin B in water (left) and formulation 22 (Amphotericin B-loaded two-polymer PLGA$_{55K}$-PEG$_{5K}$ (outer layer)/shellac (inner layer) Core-shell polymer nanoparticles (55K/SH-AB; initial DLE: 33.3%)) in water (right)
Figure 5:
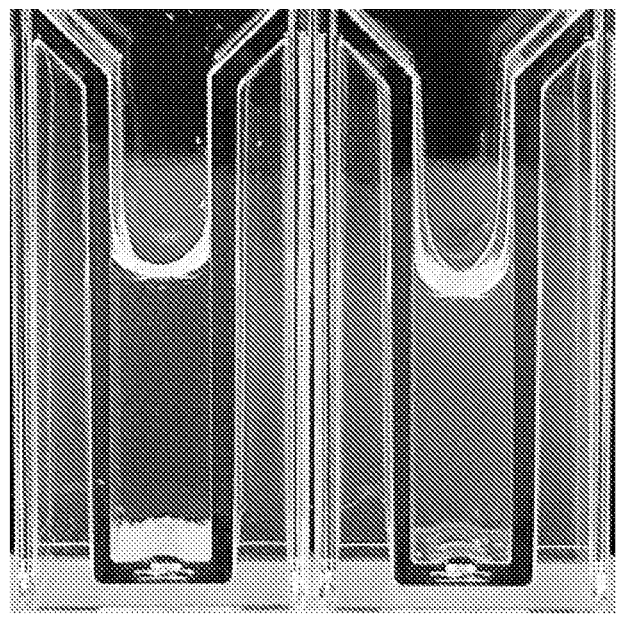
FIG. 5 is a photo of free Docetaxel (DTX) in PBS (left) and formulation 24 (Docetaxel (DTX)-loaded two-polymer PLGA$_{55K}$-PEG$_{5K}$ (outer layer)/shellac (inner layer) Core-shell polymer nanoparticles (55K/SH-DTX; initial DLE: 37.5%)) in PBS (right)

The stability of selected formulations is also detailed in tables 2 and 3 with the data indicating excellent long-term stability. The difference between the solubility, shown by cloudiness in appearance, of amphotericin B in water (left) and amphotericin B-loaded two-polymer $PLGA_{55K}$-$PEG_{5K}$ (outer layer)/shellac (inner layer) core-shell polymer nanoparticles (right) is shown in FIG. 4. The difference between the solubility, shown by cloudiness in appearance, of Docetaxel (DTX) in PBS (left) and formulation 24 (Docetaxel (DTX)-loaded two-polymer $PLGA_{55K}$-$PEG_{5K}$ (outer layer)/shellac (inner layer) core-shell polymer nanoparticles is shown in FIG. 5.

TABLE 1

Solvent systems and conditions developed for formation of core-shell polymer nanoparticles using a variety of active agent and polymer combinations (PDI is polydispersity index).

| Formulation | Polymer | Drug | Initial drug/polymer (w/w) | Optimal synthesis condition | Encapsulation efficiency (%) | Size (nm) N.M ≈ | PDI |
|---|---|---|---|---|---|---|---|
| 1 | $PLGA_{55K}$-$PEG_{5K}$ | Curcumin | 1:1 | $H_2O$ (pH 6.4) | >99 | 150 | <0.1 |
| 2 | $PLGA_{55K}$-$PEG_{5K}$ + Shellac (w/w = 5:1) | Curcumin | 1:1 | $H_2O$ (pH 6.4) | >99 | 50 | <0.2 |
| 3 | $PLGA_{55K}$-$PEG_{5K}$ + Shellac (w/w = 2:1) | Curcumin | 1:1 | $H_2O$ (pH 6.4) | >99 | 50 | <0.2 |
| 4 | $PLGA_{55K}$-$PEG_{5K}$ + Shellac (w/w = 1:1) | Curcumin | 1:1 | PBS | >99 | 65 | <0.2 |
| 5 | Shellac | Curcumin | 1:1 | $PBS/H_2O$ (pH 4~4.5) | >99 | 70 | <0.1 |
| 6 | Shellac + $PLGA_{10K}$-$PEG_{5K}$ (w/w = 5:1) | Curcumin | 1:1 | $H_2O$ (pH 4~4.5) | >99 | 70 | <0.1 |
| 7 | Shellac + $PLGA_{10k}$-$PEG_{5k}$ (w/w = 2:1) | Curcumin | 1:1 | $H_2O$ (pH 4~4.5) | >99 | 90 | <0.1 |
| 8 | Shellac + $PLGA_{10K}$-$PEG_{5K}$ (w/w = 1:1) | Curcumin | 1:1 | $H_2O$ (pH 4~4.5) | >99 | 100 | <0.1 |
| 9 | $PLGA_{10K}$-$PEG_{5K}$ | Curcumin | 1:1/3:2 | PBS | >99 | 115/160 | <0.1 |
| 10 | $PLGA_{10K}$-$PEG_{5K}$ + Shellac (w/w = 1:1) | Curcumin | 1:1 | $PBS/H_2O$ (pH 4~4.5) | >99 | 140/80 | <0.2 |
| 11 | $PLLA_{10K}$-$PEG_{5K}$ | Curcumin | 1:1 | $H_2O$ (pH 7) | >99 | 110 | <0.2 |
| 12 | Shellac | Ibuprofen | 1:1 | $H_2O$ (pH 7) | >99 | 175 | <0.1 |
| 13 | $PLGA_{10K}$-$PEG_{5K}$ | Paclitaxel | 1:1 | PBS | >95 | 110 | <0.2 |
| 14 | $PLGA_{10K}$ + $PLGA_{10K}$-$PEG_{5K}$ (w/w = 4:1) | Paclitaxel | 3:5 | PBS | >95 | 100 | <0.2 |
| 15 | $PLGA_{10K}$ | Paclitaxel | 1:1 | PBS | >93 | 60 | <0.2 |
| 16 | $PLGA_{10K}$-$PEG_{5K}$ + Shellac (w/w = 4:1) | Paclitaxel | 3:5 | PBS | >99 | 40 | <0.2 |
| 17 | $PLGA_{55K}$-$PEG_{5K}$ + Shellac (w/w = 4:1) | Paclitaxel | 3:5 | PBS | >99 | 75 | <0.2 |
| 18 | $PLGA_{55K}$-$PEG_{5K}$ + Shellac (w/w = 4:1) | Paclitaxel | 2:3 | PBS | >99 | 95 | <0.2 |
| 19 | $PLGA_{10K}$-$PEG_{5K}$ | Bulleyaconitine A | 1:1 | PBS | >99 | 100 | <0.1 |
| 20 | $PLGA_{55K}$-$PEG_{5K}$ | Ketamine | 1:1 | PBS/HEPES | >70 | 60 | <0.2 |
| 21 | $PLGA_{55K}$-$PEG_{5K}$ + Shellac (w/w = 4:1) | Ketamine | 1.2:1 | PBS/HEPES | >75 | 80 | <0.2 |

TABLE 1-continued

Solvent systems and conditions developed for formation of
core-shell polymer nanoparticles using a variety of active agent and
polymer combinations (PDI is polydispersity index).

| Formulation | Polymer | Drug | Initial drug/ polymer (w/w) | Optimal synthesis condition | Encapsulation efficiency (%) | Size (nm) N.M ≈ | PDI |
|---|---|---|---|---|---|---|---|
| 22 | PLGA$_{55K}$-PEG$_{5K}$ + Shellac (w/w = 3:1) | Amphotericin B | 1:2 | H$_2$O | >95 | 70 | <0.2 |
| 23 | PLGA$_{10K}$-PEG$_{5K}$ | Amphotericin B | 1:1 | H$_2$O | >95 | 60 | <0.2 |
| 24 | PLGA$_{55K}$-PEG$_{5K}$ + Shellac (w/w = 4:1) | Docetaxel | 3:5 | PBS/HEPES | >95 | 75 | <0.2 |
| 25 | PLGA$_{55K}$-PEG$_{5K}$ + Shellac (w/w = 3:1) | Scutellarin | 1:2 | PBS/HEPES | >95 | 70 | <0.2 |

The pH value for PBS/HEPES buffer is 7.4. Optimal solvent mixture for dissolving the polymer and drug:
1. 30% DMF + 30% DMSO + 40% ETHANOL (Formulation: 1~4, 9, 10, 19)
2. 30% DMF + 40% DMSO + 30% ETHANOL (Formulation: 5~8)
3. 30% DMF + 50% DMSO + 20% ETHANOL (Formulation: 11)
4. 50% DMSO + 50% ETHANOL (Formulation: 12)
5. 40% DMF + 20% DMSO + 40% ETHANOL (Formulation: 13~18, 20~22, 24, 25)

TABLE 2

The stability of formulation 22 in water (room temperature)

| Sample | Z-average (nm) | Number mean (nm) | Pdl |
|---|---|---|---|
| DAY 0 in water | 114 | 68.24 | 0.144 |
| DAY 1 in water | 127.2 | 95.01 | 0.145 |
| DAY 15 in water | 116.5 | 85.67 | 0.121 |

TABLE 3

The stability of formulation 24 in PBS (room temperature)

| Sample | Z-average (nm) | Number mean (nm) | Pdl |
|---|---|---|---|
| DAY 0 | 110.1 | 76.21 | 0.142 |
| DAY 1 | 111.6 | 77.34 | 0.116 |
| DAY 15 | 124.0 | 79.18 | 0.123 |
| DAY 45 | 114.7 | 75.62 | 0.133 |

Development of Further Core-Shell Polymer Nanoparticles Encapsulating Active Agents A consideration to optimise the present approach is to find the right solvent system to make the polymer precipitate quickly following the nano-drug formation caused by precipitation of the active agent. Common polymers employed in biomedical applications are PLGA/PLGA-PEG, and variations thereof, with different molecular weights and, additionally, shellac. To simplify the process of finding the optimal solvent formulation, three solvents were selected based on accessibility, toxicity and solubility of the polymer and majority of drugs. The three solvents are Dimethyl Formamide (DMF), Dimethyl sulfoxide (DMSO) and ethanol.

For most of the drugs of interest, their solubility in these three solvents is DMSO>DMF>Ethanol. Similarly, PLGA polymer is soluble in DMSO and DMF but insoluble in ethanol. However, the solubility of shellac in these three solvents is Ethanol>DMF>DMSO, which is opposite to that of PLGA and the tested drugs. Also, PLGA having a lower molecular weight has an increased precipitation time in certain solvents. For these reasons, a useful basic approach to adjust the precipitation time is to test and consider the precipitation time in DMF as the baseline. When a longer precipitation time is required, the solvent ratio can be increased for the solvent providing higher solubility and when a shorter precipitation time is required, the solvent ratio for the solvent with the lower solubility is increased.

Figure 2:
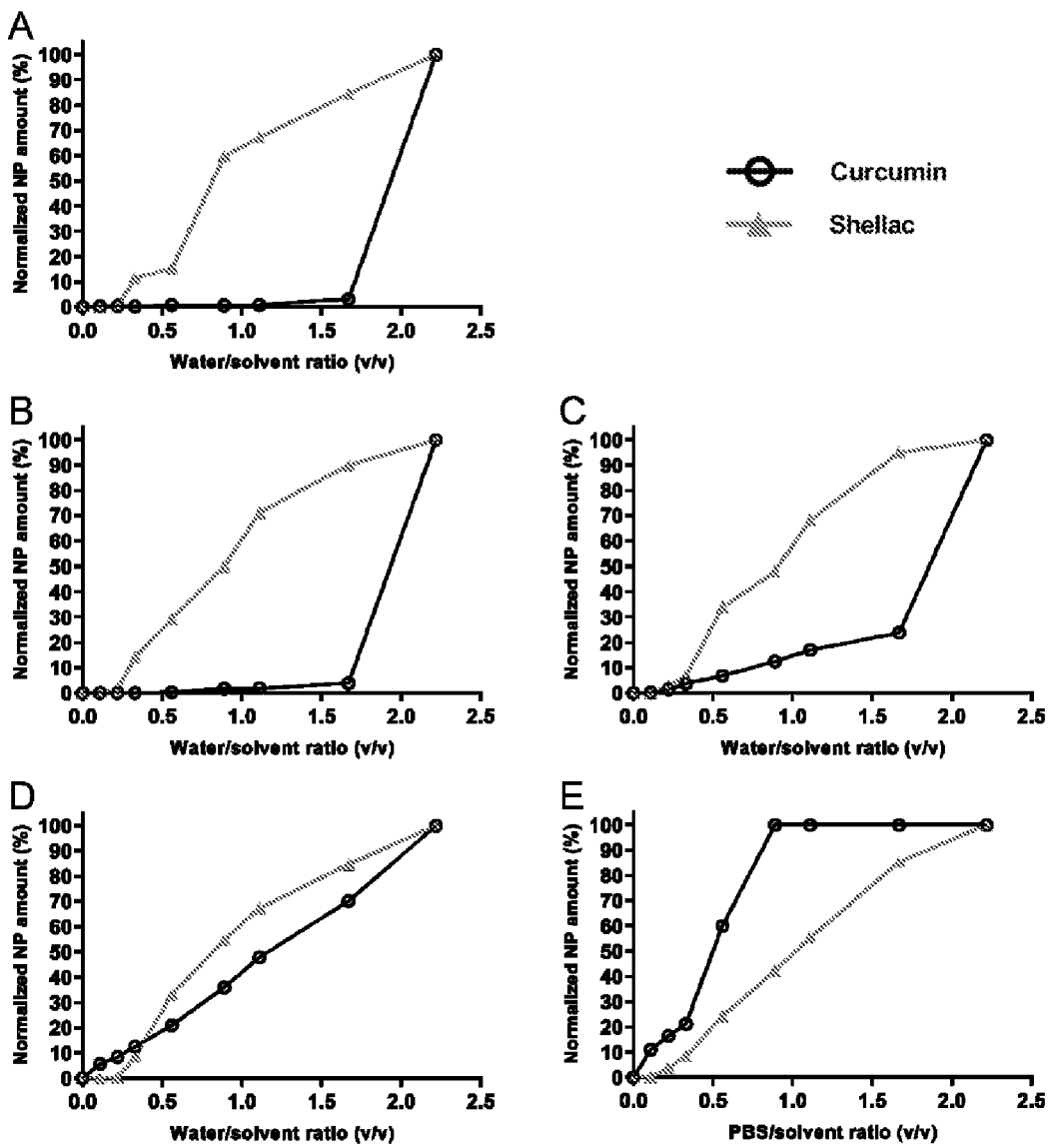
FIG. 2 is a series of graphical representations of the nanoprecipitation curves of (A) Single-solvent formulation (DMF), dual-solvent formulation with (B) DMF/DMSO (C) DMF/ETOH and an optimised tri-solvent formulation precipitated using (D) water and (E) PBS, for curcumin in shellac core-shell polymer nanoparticles.

To identify the amount of nano drug or polymeric nanoparticles formed, the Derived Count Rates (DCR) from DLS was used. Standard curves of the correlation for nanoparticle amount and DCR in PBS and water were obtained and are shown in FIG. 2. 3 mg/ml curcumin and shellac were dissolved in a single-solvent, two dual-solvent systems and a tri-solvent system to keep the drug to polymer ratio 1:1 (simulating 50% DLE). Next, water or PBS was added to the drug-containing solvent or active solution and the DCR of the solution measured to calculate the approximate nanoparticle precipitate amount based on the standard curve.

FIG. 2 shows the nanoprecipitation curves of single-solvent (DMF), dual-solvent (DMF/DMSO, DMF/Ethanol) and tri-solvent (DMF/DMSO/Ethanol) systems and the optimal formulation identified. For the single-solvent formation, when adding water, the shellac precipitated first, and almost all shellac precipitated after adding an equal amount of water (water:solvent system=1.67:1 volume ratio) (FIG. 2A). However, the majority of curcumin only started to precipitate after adding same amount of water. The large difference in precipitation timing between the polymer and curcumin explains why nanoparticles with low drug loading are obtained using a traditional one-solvent nanoprecipitation approach.

Based on FIG. 2A, it was necessary to narrow down the difference between the precipitation curves of the polymer and the drug by adjusting the parameters. The precipitation curves for curcumin and shellac were therefore further tested using two or three solvent-containing systems with various ratios. Compared to the single-solvent formulation, two solvents (DMF+DMSO or DMF+EtOH) improved the situation but it was still less than optimal (FIGS. 2B and 2C). However, when a three solvent approach was used, the precipitation curves of curcumin and shellac came significantly closer (FIG. 2D). By then using PBS instead of water, because shellac has a higher solubility in weakly alkaline conditions, it was possible to bring the curcumin curves to the left of shellac curve (FIG. 2E). This solvent combination was found to be optimal for forming shellac core-shell polymer nanoparticles with a high drug loading of curcumin. Further characterization of this curcumin loaded shellac core-shell polymer nanoparticle by DLS, TEM and DLE confirmed its high drug loading (about 50%) and drug core polymer shell structure.

In addition to natural polymers (such as shellac), synthetic polymers such as PLGA-PEG can also be used for making core-shell polymer nanoparticles with high drug loading. Various curcumin loaded Core-shell polymer nanoparticles were synthesized using 10K or 55K PLGA-PEG polymers. The maximum curcumin loading achieved with the 10K PLGA-PEG polymer was approximately 60 wt %. Similarly, the PLGA-PEG polymer can also be used for encapsulating chemotherapeutic drugs like paclitaxel (PTX) with high drug loading. But because of the different properties of shellac and PLGA-PEG, the solvent combinations used for making drug-loaded core-shell polymer nanoparticles are slightly different. For drug-loaded shellac core-shell polymer nanoparticles, a solvent combination of DMF:DMSO:Ethanol=3:4:3 (volume ratio) is used, while for PLGA-PEG, the volume ratio is 3:3:4.

Furthermore, as different polymers exhibit different stability properties, it is possible to use a mixture of two polymers or more to tune the controlled release of active agents from the active-loaded core-shell polymer nanoparticles. For example, shellac is stable in acid solution (e.g. pH 4) but swells in neutral and basic solutions, while PLGA-PEG is stable at neutral pH and swells in acid conditions. Therefore, it is possible to use polymer mixtures for forming active-loaded core-shell polymer nanoparticles. The solvent combination for different polymer mixtures will depend on the ratio of the two polymers. For example, if the formulation has more PLGA-PEG than shellac, the solvent combination for pure PLGA-PEG (DMF:DMSO:Ethanol=3:3:4 (V/V/V)) will be used. On the other hand, if the proportion of shellac is greater than that of PLGA-PEG, the combination for shellac (DMF:DMSO:Ethanol=3:4:3) is preferable.

Figure 3:
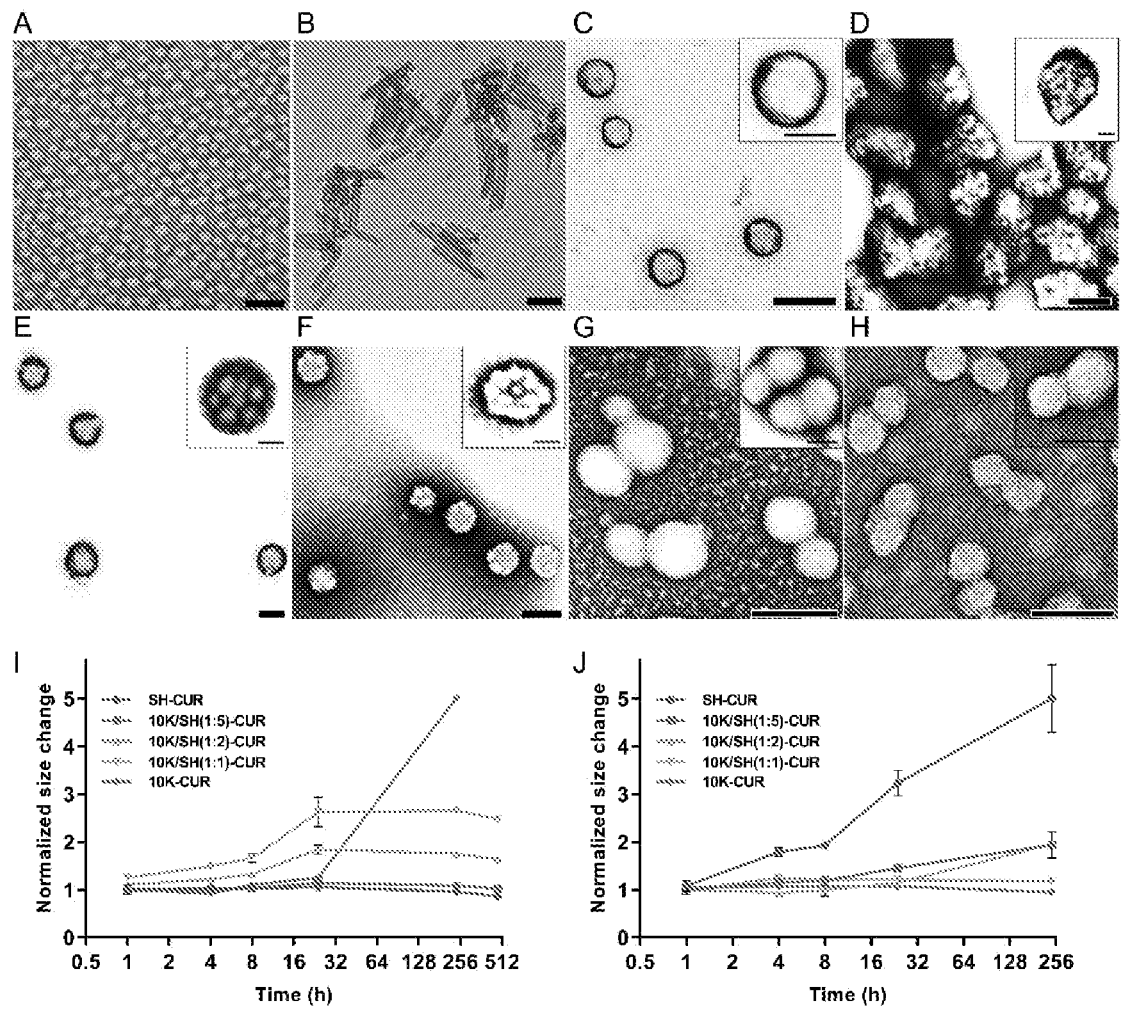
FIG. 3 (A) TEM images of (A) Nanocurcumin, (B) Curcumin crystals, (C) curcumin loaded shellac Core-shell polymer nanoparticles (SH-CUR) with 49.3% drug loading using the solvent mixture of DMSO:DMF:Ethanol of 4:3:3 (volume ratio), (D) curcumin loaded PLGA$_{55K}$-PEG$_{5K}$ Core-shell polymer nanoparticles (55K-CUR) with 49.5% drug loading using the solvent mixture of DMSO:DMF: Ethanol of 3:3:4 (volume ratio), (E) curcumin loaded PLGA$_{10K}$-PEG$_{5K}$ Core-shell polymer nanoparticles (10K-CUR) with 45.5% drug loading using the solvent mixture of DMSO:DMF:Ethanol of 3:3:4 (volume ratio), (F) curcumin loaded PLGA$_{10K}$-PEG$_{5K}$ Core-shell polymer nanoparticles (10K-CUR$_{max}$) with 58.5% drug loading, using the solvent mixture of DMSO:DMF:Ethanol of 3:3:4 (volume ratio), (G) curcumin-core shellac (inner layer)/PLGA$_{10K}$-PEG$_{5K}$ (outer layer) NPs (10K/SH-CUR) and (H) Paclitaxel-core shellac (inner layer)/PLGA$_{55K}$-PEG$_{5K}$ (outer layer) NPs (55K/SH-PTX) with 39.6% drug loading (Scale bar: 50 nm for inserts and 100 nm for whole images); Stability test of curcumin loaded nanoparticles in (I) water (pH 4.5) and (J) PBS.

FIGS. 3A-3H show TEM images for different curcumin and paclitaxel formulations. Curcumin nanoparticles (FIG. 3A) were formed by mixing a solvent system, as previously described (ethanol, DMSO, etc.), comprising dissolved curcumin with water, and the resulting nanoparticles had a uniform size of about 40 nm (FIG. 3 A), but started to form larger aggregates and crystals after 3 hours (FIG. 3B). FIG. 3C shows the formation of curcumin-loaded shellac core-shell polymer nanoparticles with about 50% drug loading, which have a particle size of about 50 nm and a very compact structure with a clear drug-core polymer-shell structure.

In contrast to curcumin-loaded shellac core-shell polymer nanoparticles (FIG. 3C), curcumin loaded PLGA-PEG Core-shell polymer nanoparticles exhibit distinct particle morphology (FIG. 3D-3F) with multiple small curcumin nanoparticles embedded in the PLGA-PEG matrix. With using $PLGA_{10K}$-$PEG_{5K}$, the drug loading can be up 60% (FIG. 3F). When a polymer mixture of PLGA-PEG and shellac was used for encapsulation of curcumin and paclitaxel, dumbbell-shape core-shell polymer nanoparticles were formed. This was probably due to the slightly larger difference in precipitation time between the drug and the two polymers. Therefore, instead of encapsulating a single drug particle, two drug particles were encapsulated inside each polymer shell.

Cytotoxicity and Anti-Tumor Activity of Drug Loaded Core-Shell Nanoparticles

Figure 6:
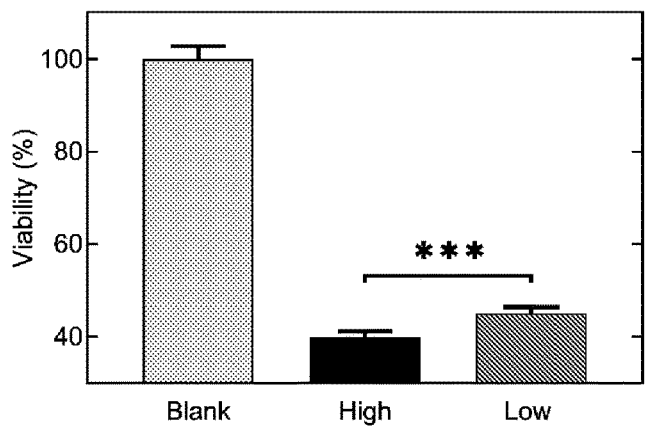
FIG. 6 is a representation of the cytotoxicity of 2D cells for PTX-loaded PLGA$_{55K}$-PEG$_{5K}$ (outer)/shellac (inner) (weight ratio 4:1) core-shell polymer nanoparticles (55K/SH (4:1)-PTX) with high (DLE: 39.6%) and low (DLE: 3.5%) drug loading (48 h, 0.9 µg/ml PTX). *, , * represent statistically significant difference (p<0.001, p<0.01, and p<0.05), ns represents no statistically significant difference (mean±SD, n=3)
Figure 7:
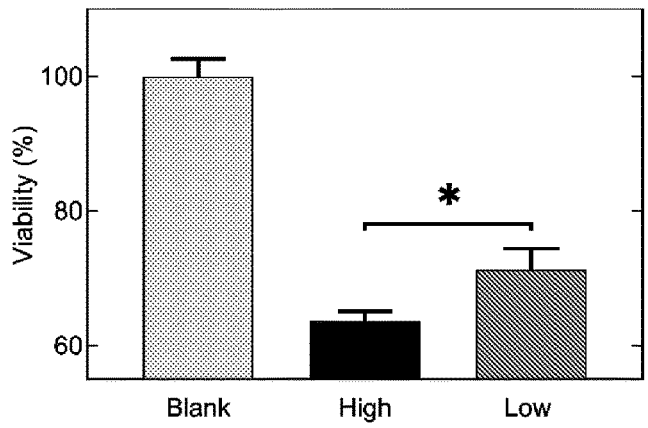
FIG. 7 is a representation of cytotoxicity of PTX-loaded PLGA$_{55K}$-PEG$_{5K}$ (outer)/shellac (inner) (weight ratio 4:1) core-shell polymer nanoparticles (55K/SH (4:1)-PTX) with high (DLE: 39.6%) and low (DLE: 3.5%) drug loading for SKOV3 tumor spheroids (72 h, 0.1 µg/ml PTX). *, , * represent statistically significant difference (p<0.001, p<0.01, and p<0.05), ns represents no statistically significant difference (mean±SD, n=3)
Figure 8:
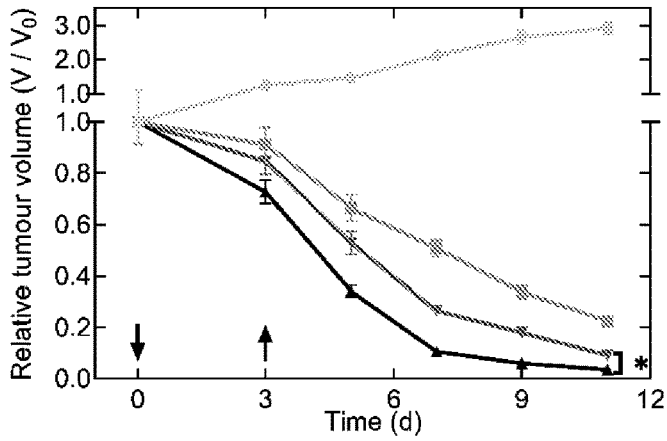
FIG. 8 is a graphical representation of tumor spheroid growth curve after incubation with PBS (the uppermost line with solid circles), free PTX (the second uppermost line with solid square) and PTX-loaded high (the lowest line with solid up triangle) and low (the third from uppermost line with solid down triangle) drug loading Core-shell polymer nanoparticles for 72 h (0.1 µg/ml PTX). Day 0 is the day of adding PTX and PTX-loaded core-shell polymer nanoparticles while Day 3 is the starting date of gradual drug removal by replacing 50% of the total medium every 48 h. *, , * represent statistically significant difference (p<0.001, p<0.01, and p<0.05), ns represents no statistically significant difference (mean±SD, n=5)
Figure 9:
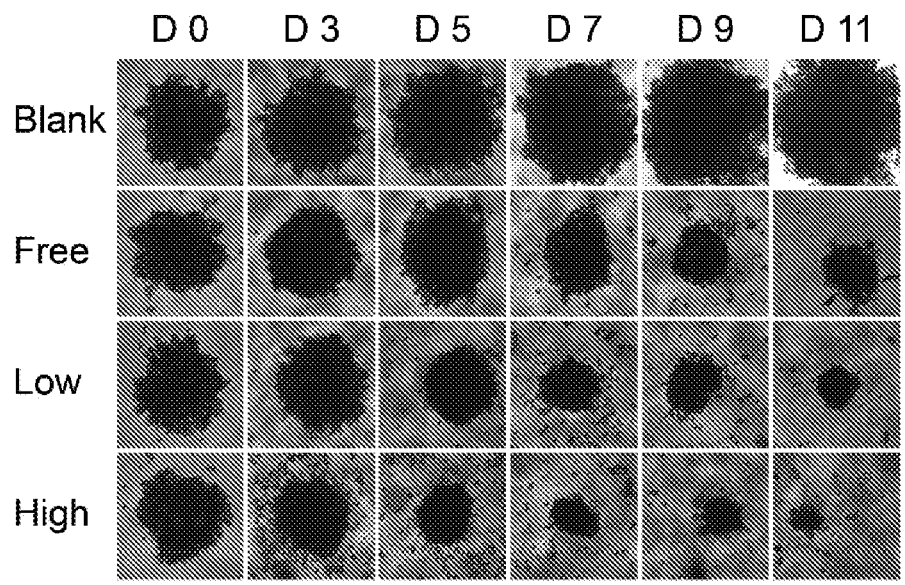
FIG. 9 is a series of images of corresponding tumor spheroid morphology (relating to the results of FIG. 8) during the tumor spheroid growth after incubation of the PBS, free PTX and PTX-loaded high and low drug loading core-shell polymer nanoparticles for 72 h (0.1 µg/ml PTX). Day 0 is the day of adding PTX and PTX-loaded core-shell polymer nanoparticles while Day 3 is the starting date of gradual drug removal by replacing 50% of the total medium every 48 h.

To compare the cell cytotoxicity of core-shell polymer nanoparticles of the invention with high and low drug loading, two types were synthesized, namely, PTX-loaded core-shell polymer nanoparticles ($PLGA_{55K}$-$PEG_{5K}$ and shellac at a mass ratio of 4:1) with high drug loading (39.6%) and low drug loading (3.5%). The PTX-loaded core-shell polymer nanoparticles with high drug loading showed reduced cell viability compared to those with low drug loading in both 2D-monolayer cells (FIG. 6) and 3D-tumor spheroids (FIG. 7). Further, the growth curves of the tumor spheroids incubated with PTX-loaded high and low drug core-shell polymer nanoparticles were monitored for 11 days. Compared to the spheroids treated with free PTX and low drug loading core-shell polymer nanoparticles, those spheroids treated with the high drug loading core-shell polymer nanoparticles showed persistent volume decrease, indicating its significant anti-tumor effect (FIG. 8), consistent with the tumor spheroid morphology seen during the incubation period (FIG. 9).

Figure 10:
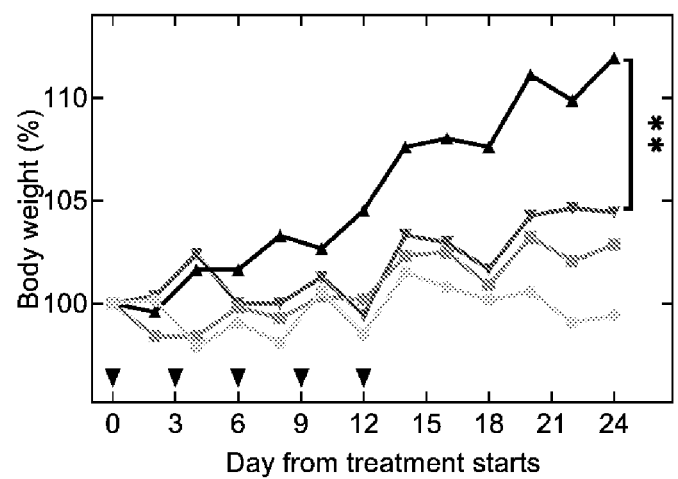
FIG. 10 is a graphical representation of the body weight of tumor-bearing mice during 24 days since 1$^{st}$ injection (Day 0) for PBS (the lowermost trace when looking at rightmost data point, solid circle), Free PTX (the second trace from the lowest when looking at rightmost data point, solid square), High DL NP (the uppermost trace when looking at rightmost data point, solid up triangle), and Low DL NP (second from the uppermost trace when looking at rightmost data point, solid down triangle) groups. Five injections in total at day 0, 3, 6, 9 and 12. *, , * represent statistically significant difference (p<0.001, p<0.01, and p<0.05), ns represents no statistically significant difference (mean±SD, n=5~6)
Figure 11:
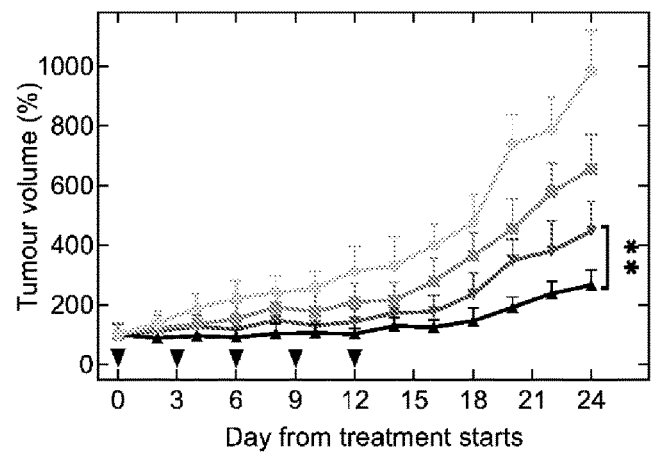
FIG. 11 is a graphical representation of the tumor volume of tumor-bearing mice during 24 days since 1$^{st}$ injection (Day 0) for PBS (the uppermost line with solid circles), Free PTX (the second from uppermost line with solid square), High DL NP (the lowest line with solid up triangle), and Low DL NP (the second from lowest line with solid down triangle) groups. Five injections in total at day 0, 3, 6, 9 and 12. *, , * represent statistically significant difference (p<0.001, p<0.01, and p<0.05), ns represents no statistically significant difference (mean±SD, n=5~6)
Figure 12:
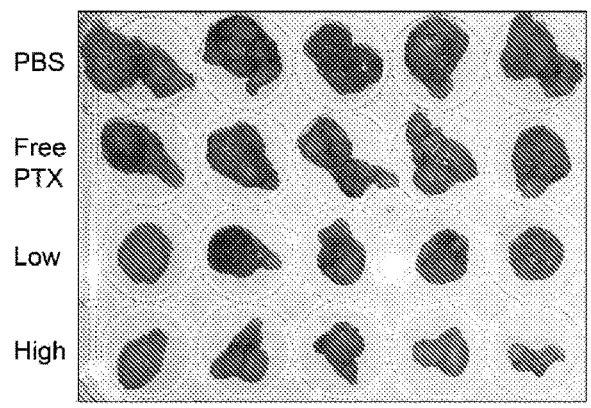
FIG. 12 is a series of tumor images isolated from tumor-bearing mice after treatment with PBS, free PTX, Low and High drug loading core-shell polymer nanoparticles.

In vivo mice experiments were conducted to evaluate the anti-tumor therapeutic effects of PTX-loaded high (55K/SH-PTX; 39.6% drug loading) and low-drug loading formulations (55K/SH-PTX; 3.5% drug loading) in tumor-bearing mice. Four formulations (PBS, Free PTX, High DL NP, and Low DL NP—where DL is drug loading and NP is core-shell polymer nanoparticle) were injected intravenously every 72 hours for 5 injections in total. The body weight and tumor volume of the mice were monitored every two days. The body weight and tumor volume growth curves are displayed in FIGS. 10 and 11 respectively. The mice treated with High DL NP had a body weight increase of 12.0% at day 25 compared to day 0 post-injection. The weight increase was higher than the Low DL NP group (4.4% increase) and Free PTX group (2.9% increase). In contrast, the tumor volume of High DL NP group was much smaller than other groups (FIGS. 11 and 12), at day 24 post-injection.

Figure 13:
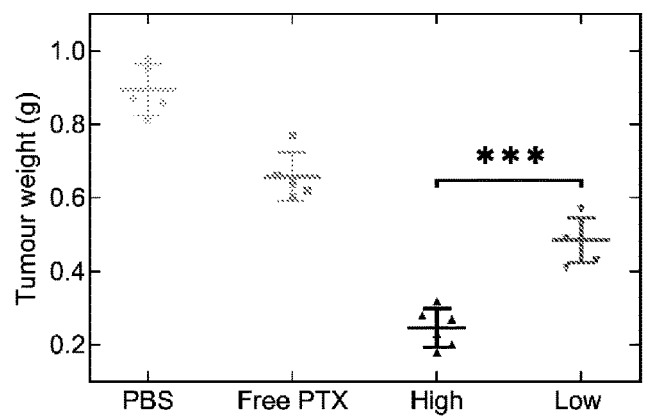
FIG. 13 is a representation of the tumor weight of isolated tumors of tumor-bearing mice after treatment of PBS, free PTX, Low and High drug loading core-shell polymer nanoparticles. *, , * represent statistically significant difference (p<0.001, p<0.01, and p<0.05), ns represents no statistically significant difference (mean±SD, n=5~6)

All results indicate that the tumor inhibition effect of High DL NPs was much better than that of Low DL NPs and Free PTX despite that all provided for the same amount of the anticancer drug PTX. The weight of the excised tumors shows a similar trend (FIG. 13). The mean tumor weight of the High DL NPs group (0.25 g) was significantly lower than the Low DL NP (0.49 g). Additionally, the High DL NP used less polymer resulting in a much lower particle concentration when injecting the same dose of the drug. The lower NP concentration provides for further advantages in use such as less polymer/time consumption during synthesis and easier injection due to the lower viscosity of the High DL NP suspension which reduces the probability of blood vessel blockage.

Figure 14:
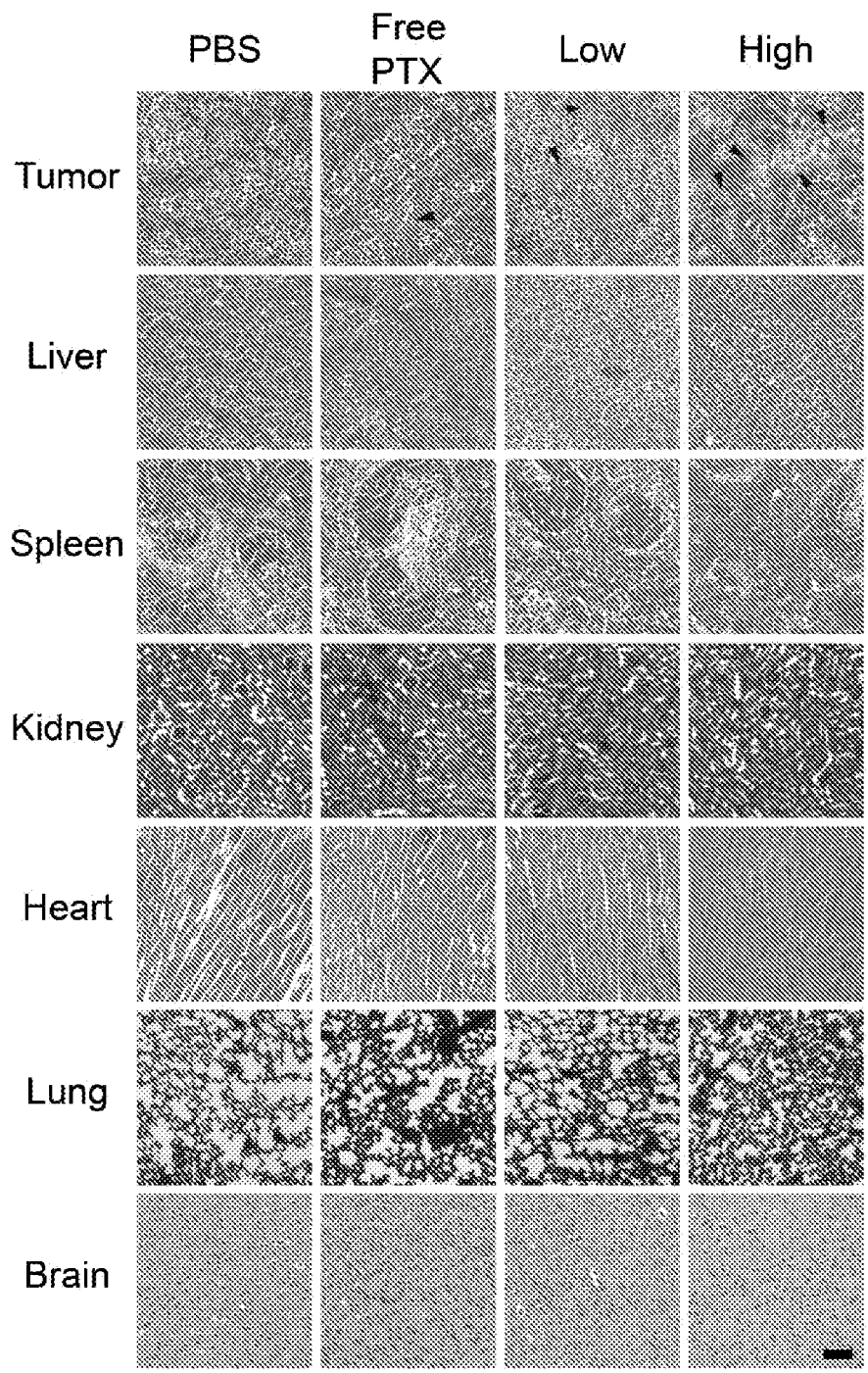
FIG. 14 is a series of histological H&E staining images of tumors and the main organs (liver, spleen, kidney, heart, lung and brain) of mice after treatment with PBS, free PTX, Low and High drug loading core-shell polymer nanoparticles.

The histopathological analysis of tumor and main organs (FIG. 14) shows that the necrosis of tumor tissue increases and the proliferation of tumor cells slows down in all treatment groups but with the High DL NP group displaying the most tumor tissue necrosis. The High DL NP group also illustrated its high safety and low side effect behaviour in the continually increased body weight and the absence of signs of necrosis or cell death in the liver, spleen or kidney, heart, lung, and brain. The in vivo results show the High DL NP formulation has a higher anti-tumor efficacy than the Low DL NP and Free PTX, while also demonstrating high safety and low side effects. This indicates the advantages of the present approach to provide for a higher drug-loading core-shell nanoparticle than is achievable by traditional methods known in the art.

In the claims which follow and in the preceding description of the invention, except where the context clearly requires otherwise due to express language or necessary implication, the word "comprise", or variations thereof including "comprises" or "comprising", is used in an inclusive sense, that is, to specify the presence of the stated integers but without precluding the presence or addition of further integers in one or more embodiments of the invention.

The invention claimed is:

1. A method of forming a core-shell polymer nanoparticle comprising an active agent including the steps of:
   (a) dissolving a polymer and an active agent in a solvent system, the solvent system comprising at least two organic solvents, to thereby form an active solution; wherein the w/w ratio of the active agent to the polymer (being the total polymer content) in the active solution is between 5:1 to 1:5; wherein the solvents forming the solvent system are at least two of DMSO, DMF and ethanol; and
      wherein when DMSO is present, it forms between 20% to 60% (v/v) of the solvent system;
      wherein when DMF is present, it forms between 20% to 45% (v/v) of the solvent system; and
      wherein when ethanol is present, it forms between 10% to 50% (v/v) of the solvent system;
   (b) mixing the active solution with at least one antisolvent to precipitate the active agent and the polymer; wherein the antisolvent is a polar solvent, and comprises an aqueous solution; wherein the ratio of antisolvent to solvent system is between about 5:1 to about 50:1; and
   (c) allowing the precipitated polymer and active agent to form a core-shell polymer nanoparticle comprising the active agent.

2. The method of claim 1 wherein the polymer is a natural or synthetic biocompatible polymer.

3. The method of claim 2 wherein the natural polymer is a resin.

4. The method of claim 1 wherein the polymer is a block copolymer.

5. The method of claim 4 wherein the polymer is an amphiphilic block copolymer.

6. The method of claim 1 wherein the polymer is at least two polymers.

7. The method of claim 1 wherein the active agent is selected from an anti-infective, antimalarial, antiviral, antibiotic, antifungal, antioxidant, antiprotozoal, antineoplastic, cardiovascular agent, antihypertensive, analgesic, anticoagulant, antidepressant, antiarthritic, antipsychotic, neuroprotective, radiologic, respiratory agent, anti-cancer, anti-migraine and antipyretic.

8. The method of claim 6 wherein the active agent is selected from taxol (paclitaxel), taxol derivatives including docetaxel, doxorubicin, bulleyaconitine A, amphotericin B, scutellarin, quercetin, silibinin, oleanolic acid, betulinic acid, honokiol, camptothecin, camptothecin derivatives, curcumin and curcumin derivatives, ibuprofen and ketamine.

9. The method of claim 1 wherein the solvent system comprises at least three organic solvents.

10. The method of claim 1 wherein the majority of the solvent system comprises DMSO and/or DMF.

11. The method of claim 1 wherein the antisolvent is water.

12. The method of claim 1, wherein when DMF is present, it forms between 25% to 40% (v/v) of the solvent system.

13. The method of claim 1, wherein when DMSO is present, it forms between 25% to 55% (v/v) of the solvent system.

14. The method of claim 1, wherein when ethanol is present, it forms between 30% to 50% (v/v) of the solvent system.

* * * * *